(12) United States Patent
Mayweather

(10) Patent No.: US 6,318,997 B1
(45) Date of Patent: Nov. 20, 2001

(54) SYSTEM FOR FORMING DENTAL IMPRESSIONS

(76) Inventor: George S. Mayweather, 8013 Laguna Blvd., Suite 1, Elk Grove, CA (US) 95758

( * ) Notice: Subject to any disclaimer, the term of this patent is extended or adjusted under 35 U.S.C. 154(b) by 0 days.

(21) Appl. No.: 09/505,569

(22) Filed: Feb. 17, 2000

(51) Int. Cl.[7] ........................................ A61C 9/00
(52) U.S. Cl. ........................ 433/45; 433/34; 433/37; 433/77; 433/229; 264/16
(58) Field of Search .................. 433/34, 37, 45, 433/77, 213, 214, 229; 206/63.5; 264/16, 17, 18

(56) References Cited

U.S. PATENT DOCUMENTS 3,360,860 * 1/1968 Roland .................................. 433/45
5,647,744 * 7/1997 Squicciarini ........................... 433/34

* cited by examiner

*Primary Examiner*—John J. Wilson
(74) *Attorney, Agent, or Firm*—Thomas R. Lampe

(57) ABSTRACT

A block member is selectively positioned on a dental impression tray with an outer engagement surface of the block member in engagement with the tray portion defining a lingual recess to block entry of plaster or other casting material into the lingual recess.

12 Claims, 4 Drawing Sheets

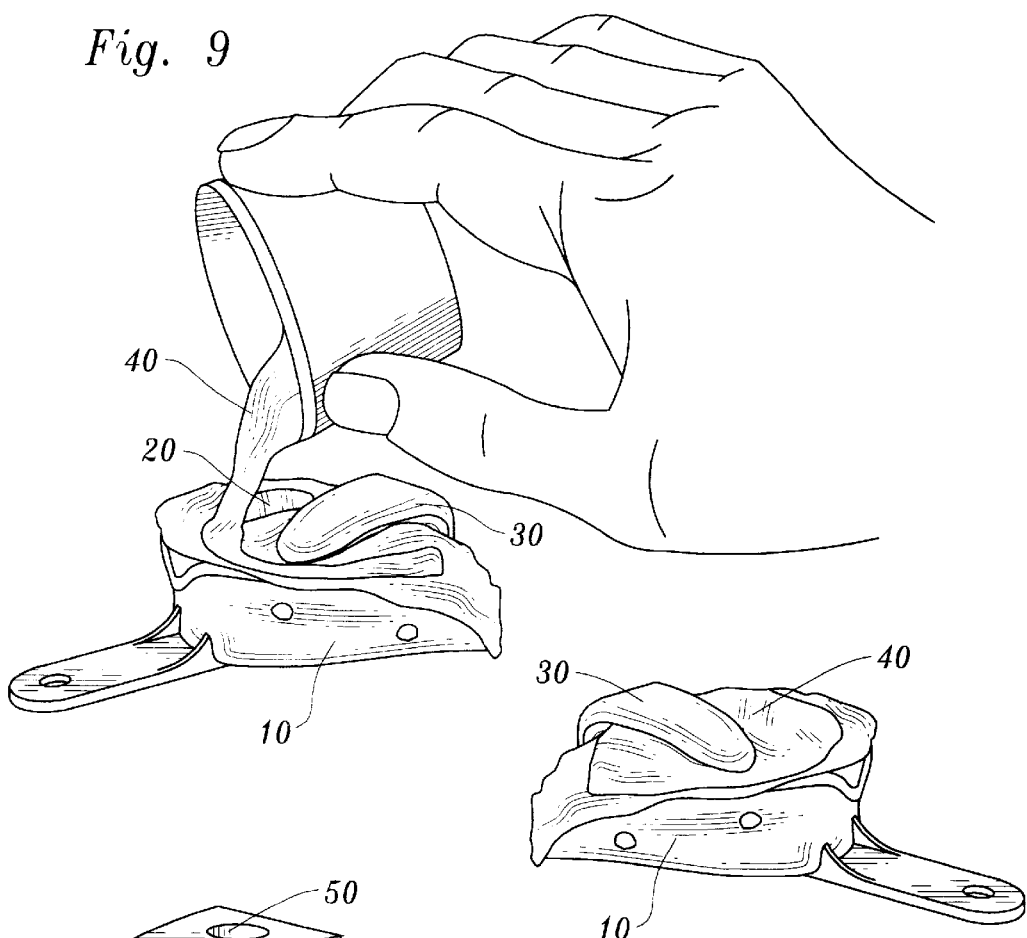
Fig. 9
Fig. 10
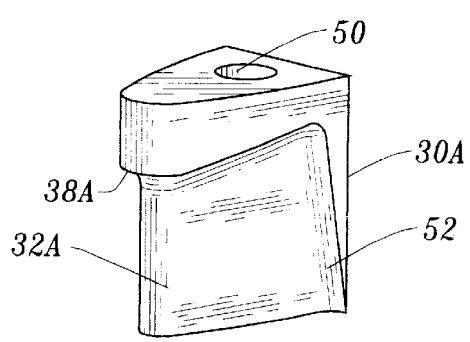
Fig. 11
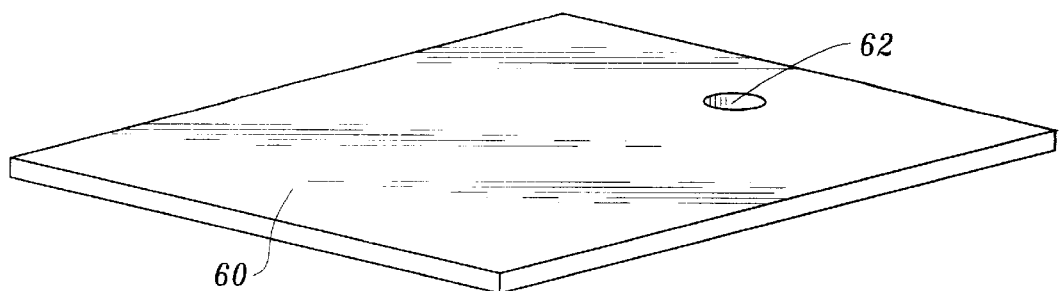
Fig. 12

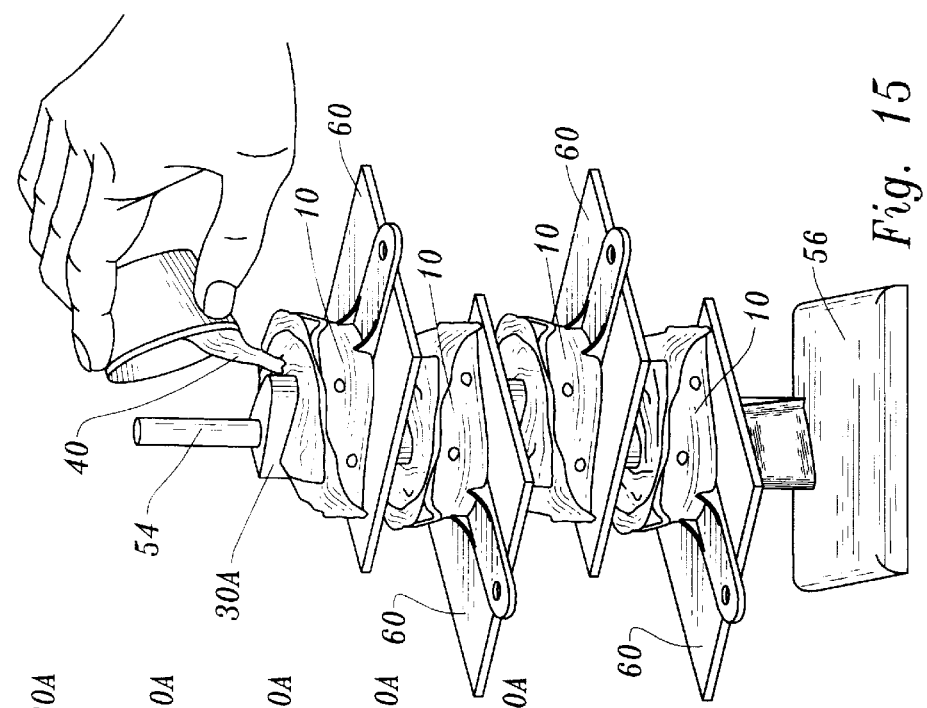
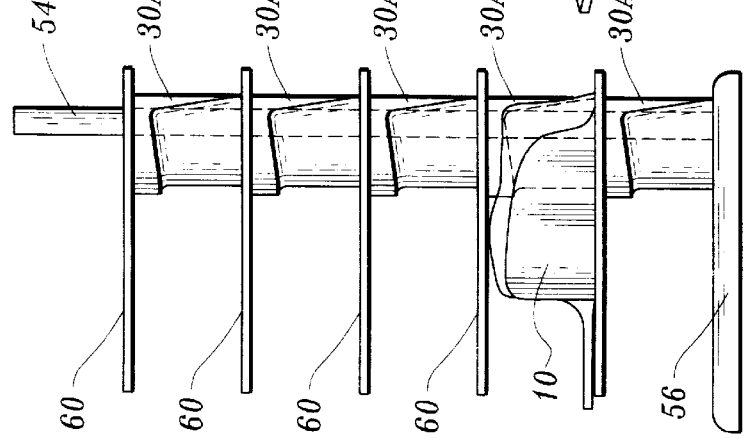
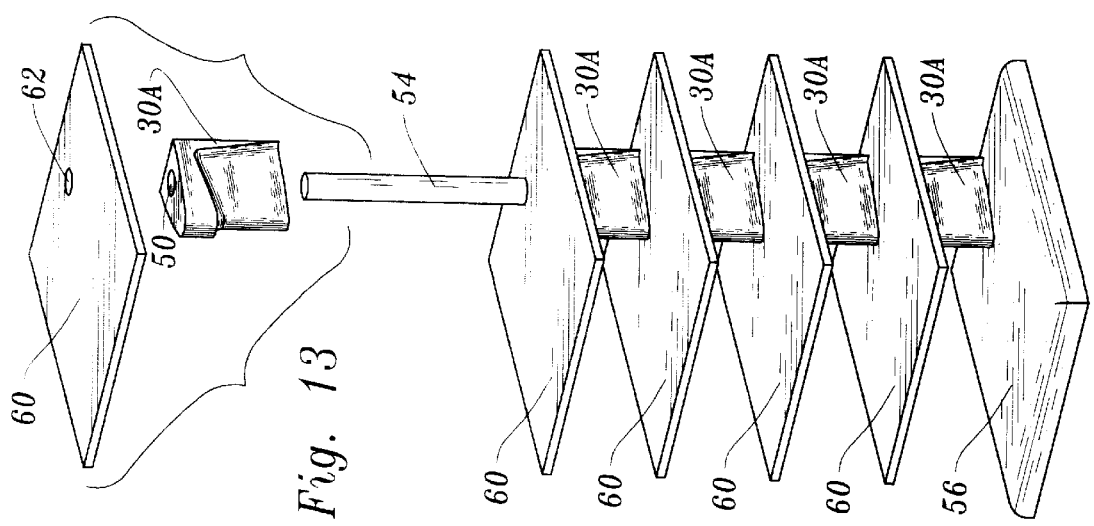
Fig. 13
Fig. 14
Fig. 15

SYSTEM FOR FORMING DENTAL IMPRESSIONS

TECHNICAL FIELD

This invention relates to the dental arts, and more particularly to an apparatus and method employed when taking dental impressions and making casts of the impressions.

BACKGROUND OF THE INVENTION

Dental impression trays are widely used to take teeth impressions and form casts from the impressions. Dental impression trays form a concavity or interior in which soft impression material is placed. The impression tray and impression material are then introduced into a patient's mouth. An impression is made by the dentist positioning the impression tray and impression material over the patient's teeth and applying pressure so that the impression material disperses around the teeth and dental arch.

The dental impression tray and impression material are removed from the patient's mouth after the impression is made. The next step in the process is to pour plaster or other casting material into the impression and into the interior of the dental impression tray.

Lower dental impression trays typically define a lingual recess to accommodate a patient's tongue during the taking of an impression and it is not uncommon for the plaster or other casting material to flow over the tray and into the lingual recess, resulting in an unsightly appearance and improper lingual representation. It is desirable when taking orthodontic impressions that the final model be smooth and accurate.

DISCLOSURE OF INVENTION

The present invention relates to a system which provides an easy to use, effective means for eliminating the problems noted above. The invention is characterized by its simplicity and its relatively low cost.

The invention encompasses a device for use with a dental impression tray having a tray top, a tray bottom and a tray portion defining a lingual recess to block entry of plaster or other casting material into the lingual recess when a cast is being made in the dental impression tray.

The device comprises a block member including an outer engagement surface, the block member being selectively positionable in the lingual recess of a dental impression tray with the outer engagement surface thereof in engagement with the tray portion defining the lingual recess or removable from the lingual recess.

The block member is of a size and configuration to be releasably retained in the lingual recess due to frictional engagement between the dental impression tray and the block member.

The invention also encompasses a method of forming a dental cast. The method includes the step of taking an impression of an individuals teeth by pressing the teeth into impression material disposed in a dental impression tray having a tray top, a tray bottom and a tray portion defining a lingual recess.

After the step of taking the impression, a block member is placed into the lingual recess of the dental impression tray.

The block member is brought into engagement with the dental impression tray while the block member is in the lingual recess of the dental impression tray.

During engagement between the block member and the dental impression tray, the block member is releasably retained on the dental impression tray due to frictional engagement between the block member and the dental impression tray.

While the block member is releasably retained on the dental impression tray, a cast is formed by filling the impression with casting material.

The block member is employed to block entry of the casting material into the lingual recess of the dental impression tray during the step of forming a cast.

Other features, advantages, and objects of the present invention will become apparent with reference to the following description and accompanying drawings.

BRIEF DESCRIPTION OF DRAWINGS

FIG. 9 illustrates the formation of the cast of the teeth impressions in the impression material disposed in the tray;

FIG. 10 illustrates the casting material in place to form a mold;

FIG. 11 is a perspective view illustrating an alternative embodiment of the block member;

FIG. 12 is a perspective view of a support plate utilized to stack a plurality of block members;

FIG. 13 is a perspective view illustrating a mounting post holding a plurality of support plates and block members in the stacked relationship;

FIG. 14 is a side view of the mounting post, a plurality of support plates and block members stacked thereon, one of the block members having a dental impression tray attached thereto; and FIG. 15 illustrates a plurality of support plates on the mounting post, each support plate associated with a dental impression tray and cast.

MODES FOR CARRYING OUT THE INVENTION

Figure 1:
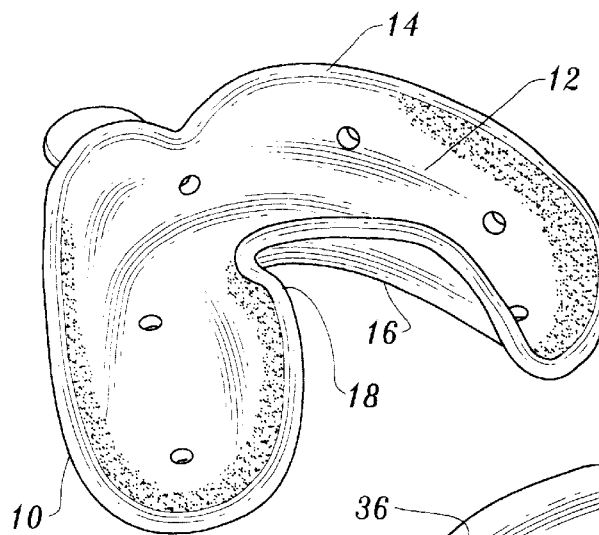
FIG. 1 is a top perspective view of a conventional dental impression tray.

FIG. 1 illustrates a conventional dental impression tray utilized to take dental impressions. The dental tray is designated by reference number 10. The dental impression tray is typically constructed of plastic or metal material and includes a tray interior 12, a tray top 14 and a tray bottom 16. The tray 10 includes a tray portion defining a tray recess 18 for accommodating an individual's tongue when taking an impression.

Figure 5:
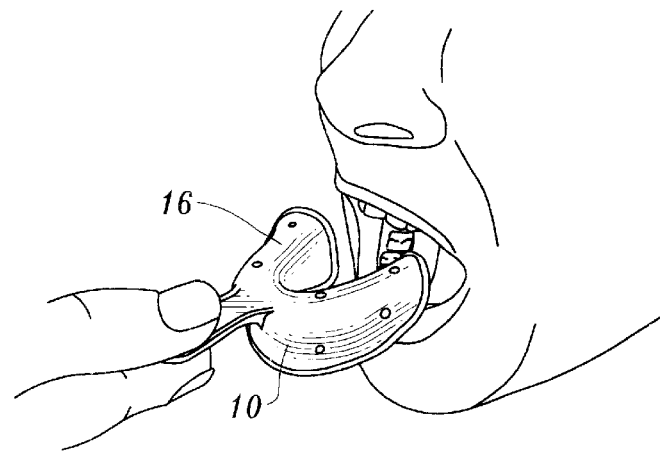
FIG. 5 is a perspective view illustrating a dental impression tray inverted and being positioned in a patient's mouth to take an impression of the patient's lower teeth.

FIG. 5 illustrates the tray being inserted into a patients mouth. In the figure, the tray has been inverted so that the tray bottom 16 is disposed upwardly. It will be appreciated that the tray interior accommodates a teeth impression material such as wax.

Figure 6:
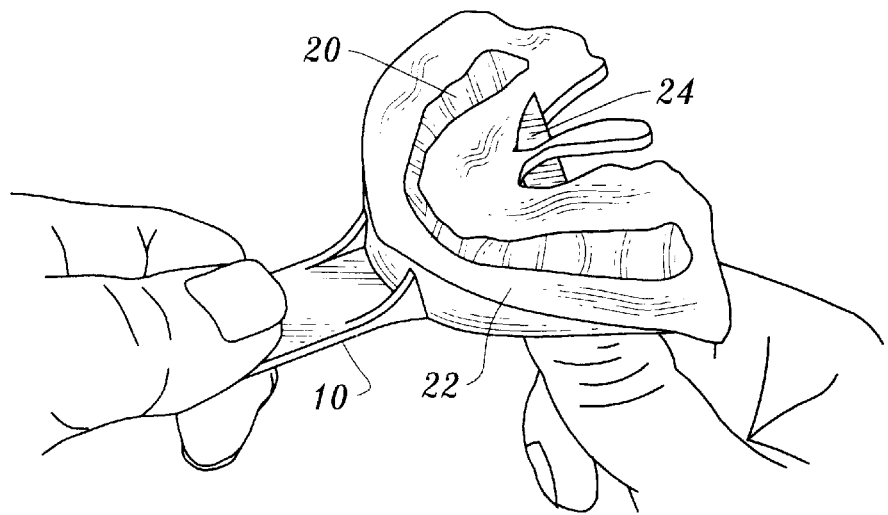
FIG. 6 is a perspective view illustrating the unwanted (excess) impression material being trimmed from the lingual recess area of the tray.

After the impression has been made by virtue of the dentist pressing the patient's teeth into the impression material, the tray and impression material are removed from the mouth. FIG. 6 illustrates the dental impression tray top side up and an impression 20 formed in the impression material 22. In FIG. 6 a knife 24 is being used to trim away excess impression material from the lingual recess of the dental impression tray.

Figure 7:
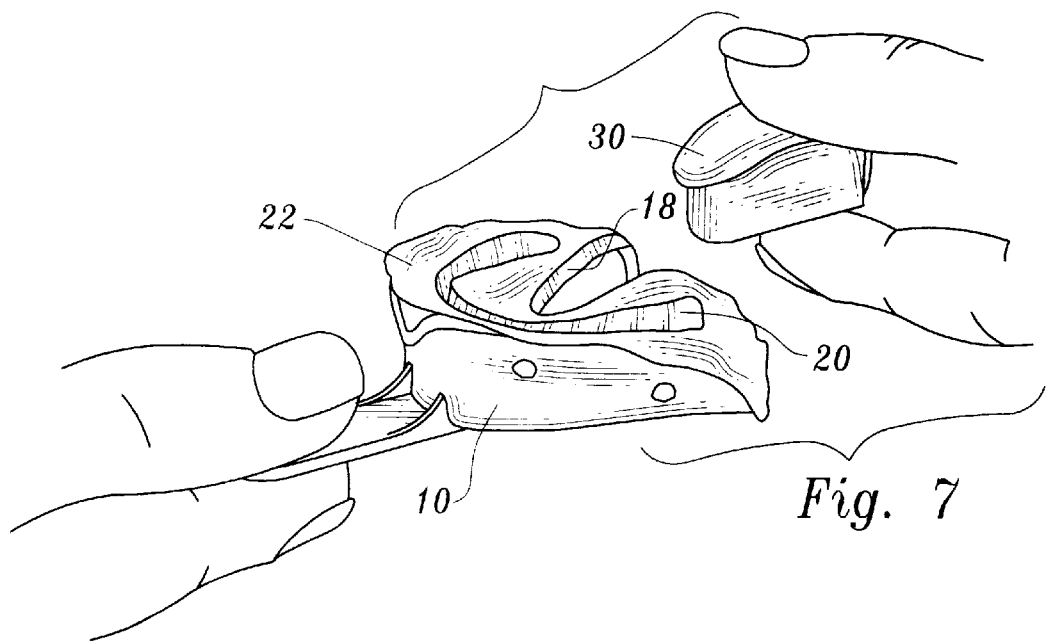
FIG. 7 is a perspective view illustrating the block member being positioned for entrance into the lingual recess of the tray.
Figure 8:
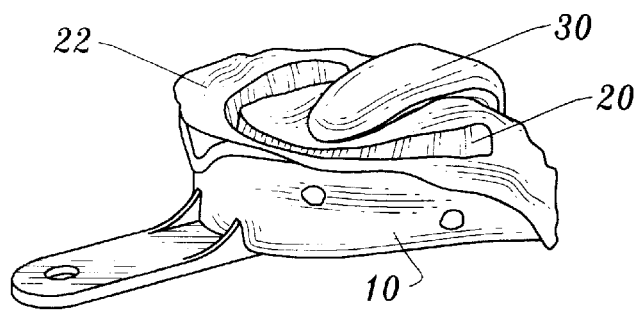
FIG. 8 illustrates the block member positioned in the lingual recess and connected to the dental impression tray.

The next step is shown in FIG. 7 wherein a block member 30 is placed into the lingual recess 18 and then brought into engagement with the dental impression tray and impression material as shown in FIG. 8.

Figure 2:
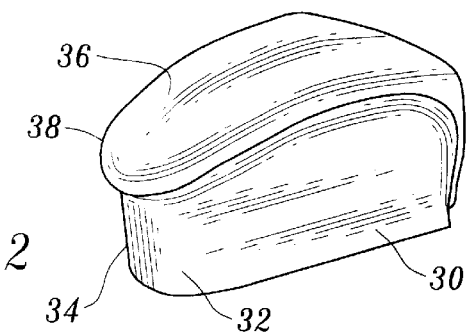
FIG. 2 is a perspective view of the block member of the present invention.
Figure 3:
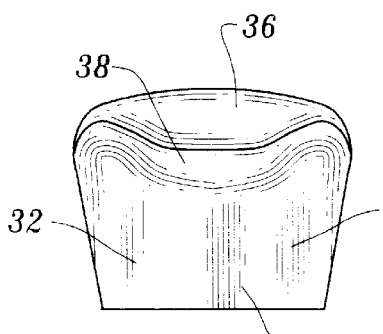
FIG. 3 is a front elevational view of the block member.
Figure 4:
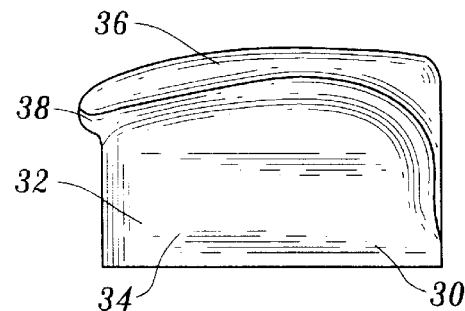
FIG. 4 is a right side view of the block member.

The structure of the block member 30 may perhaps best be seen with reference to FIGS. 2, 3 and 4. The block member 30 is of unitary and compressible construction, being formed, for example, of styrofoam. The block member 30 has a curved outer engagement surface 32 on a primary block member segment 34.

The block member 30 also includes a secondary block member segment 36 internal with the primary block member segment and including an outwardly projecting lip 38 extending beyond the curved outer engagement surface 32.

The block member 30 is of a size and configuration to be releasably retained in the lingual recess due to frictional engagement between the dental impression tray and the block member.

More particularly, the dimensions of the curved outer engagement surface 32 of primary block segment 34 are greater than the corresponding dimensions of the lingual recess where the surface 32 engages the tray. Thus, when the block member 30 is pushed into place in the lingual recess and into engagement with the dental impression tray, compressive forces will be applied to the block member. This will result in the block member being releasably retained in the lingual recess due to frictional engagement between the dental impression tray and the block member. At the same time the lip 38 will be positioned over the top of the tray portion defining the lingual recess and in engagement with either the tray or impression material to further stabilize the block member relative to the tray.

FIG. 9 shows the block member 30 retained in position on the dental impression tray while plaster or other casting material 40 is being poured into impression 20 to initiate formation of a cast. The block member 30 will prevent the casting material from entering or spilling over into the lingual recess.

For orthodontic impressions or impressions where the final impression needs to be smooth, the transition area from the impression material to the block member can be smoothed by hand or tool between the block member and the impression. The block member can also be used as a template with alginate being smoothed from one side to the other and over the top of the block member so that the tongue area can be shaped more accurately to whatever the preference.

FIG. 10 shows the casting material in the dental impression tray and confined by the block member. Once the casting material has been poured and set, the block member can be left upright or inverted.

FIGS. 11–15 illustrate another embodiment of the invention, FIG. 11 illustrating a block member 30A configured somewhat differently than block member 30. The block member 30A defines a mounting hole 50 passing there-through. Block member 30A is taller than block member 30 and includes a pair of abutment surfaces 52, only one of which is shown in FIG. 11, for abuttingly engaging a dental impression tray when the block member is releasably retained in the lingual recess thereof.

FIG. 13 shows a plurality of block members 30A stacked on a mounting post 54 extending upwardly from a base 56. Support plates 60, each having a mounting aperture 62 for receiving post 54, are disposed between adjacent stacked block members 30A, the mounting apertures 62 and the mounting holes 50 being aligned and receiving the mounting post. FIG. 13 illustrates several block members 30A and support plates 60 in stacked relationship and one block member and support plate being positioned for mounting on the mounting post.

This arrangement provides a convenient approach for stacking a plurality of dental impression trays. FIG. 14 shows one tray 10 in position and attached to a block member 30A. FIG. 15 shows four such trays, the topmost tray receiving poured casting material 40. The support plates 60 and the dental impression trays supported thereby may be turned on the mounting post as shown in FIG. 15 to provide access to the trays for cast pouring or other purposes. It will be appreciated that the trays and block members with which they are associated may be added or removed from the stack either separately or as a unit, as desired.

What is claimed is:

1. A device for use with a dental impression tray having a tray top, a tray bottom and a tray portion defining a lingual recess to block entry of plaster or other casting material into the lingual recess when a cast is being made in the dental impression tray, said device comprising a block member including an outer engagement surface, said block member being selectively positionable in the lingual recess of a dental impression tray with the outer engagement surface thereof in engagement with the tray portion defining the lingual recess or removable from the lingual recess, said block member being of a size and configuration to be releasably retained in the lingual recess due to engagement between said dental impression tray and said block member, said block member being of unitary and compressible construction and said block member including a primary block member segment having said outer engagement surface, said outer engagement surface being curved, and a secondary block member segment attached to said primary block member segment and including an outwardly projecting lip extending beyond said outer engagement surface and positioned over said tray top when said block member is releasably retained in the lingual recess due to frictional engagement between said dental impression tray and said block member.

2. The device according to claim 1 wherein said block member defines a mounting hole for mounting the block member and a dental impression tray connected thereto on a mounting post.

3. The device according to claim 1 wherein said block member includes at least one abutment surface for abuttingly engaging the dental impression tray or teeth impression material in the tray when said block member is releasably retained in the lingual recess thereof.

4. In combination:
   a dental impression tray having a tray top, a tray bottom and a tray portion defining a lingual recess; and
   a device for blocking entry of plaster or other casting material into the lingual recess of the dental impression tray when a cast is being made in the dental impression tray, said device comprising a block member having an outer engagement surface, said block member being at least partially formed of compressible material and releasably retained in the lingual recess due to engagement between said dental impression tray and said block member with the outer engagement surface of said block member sealingly engaging said dental impression tray at said lingual recess, said block member including an outwardly projecting lip disposed above said outer engagement surface engaging said tray top or teeth impression material in the tray.

5. A method of forming a dental cast, said method comprising the steps of:

taking an impression of an individual's teeth by pressing the teeth into impression material disposed in a dental impression tray having a tray top, a tray bottom and a tray portion defining a lingual recess;

after the step of taking the impression, placing a block member into the lingual recess of said dental impression tray;

bringing the block member into engagement with the dental impression tray while the block member is in the lingual recess of said dental impression tray;

during engagement between the block member and the dental impression tray releasably retaining the block member on the dental impression tray due to engagement between said block member and the dental impression tray;

while said block member is releasably retained on said dental impression tray, forming a cast by filling the impression with casting material;

employing the block member to block entry of said casting material into the lingual recess of said dental impression tray during the step of forming a cast; and removing the block member from the dental impression tray after the step of forming a cast, the step of releasably retaining the block member on the dental impression tray being accomplished by applying compressive forces to the block member with the dental impression tray.

6. The method according to claim 5 including the additional step of removing any impression material in the lingual recess after the step of taking an impression and prior to bringing the block member into engagement with the dental impression tray.

7. The method according to claim 5 wherein the step of forming a cast includes pouring fluent casting material into the impression and hardening the casting material, said block member being removed from the dental impression tray after hardening of the casting material.

8. In combination:

a dental tray having a tray top, a tray bottom and a tray portion defining a lingual recess;

a device for blocking entry of the plaster or other casting material into the lingual recess of the dental impression tray, said device comprising a block member being at least partially formed of compressible material and releasably retained in the lingual recess due to engagement between dental impression tray and said block member, with the outer surface of said block member sealingly engaging said dental impression tray at said lingual recess; and a mounting post for mounting the dental impression tray and the block member at a predetermined location, said block member defining a mounting hole for receiving the mounting post.

9. The combination according to claim 8 wherein said mounting post mounts the dental impression tray and block member in stacked relationship with at least one additional dental tray and block member.

10. The combination according to claim 9 additionally comprising a plurality of support plates stacked on said mounting post, at least one of said plates being disposed between adjacent stacked block members.

11. A device for use with a dental impression tray having a tray top, a tray bottom and a tray portion defining a lingual recess to block entry of plaster or other casting material into the lingual recess when a cast is being made in the dental impression tray, said device comprising a block member including an outer engagement surface, said block member being selectively positionable in the lingual recess of a dental impression tray with the outer engagement surface thereof in engagement with the tray portion defining the lingual recess or removable from the lingual recess, said block member being of a size and configuration to be releasably retained in the lingual recess due to engagement between said dental impression tray and said block member, said block member being of unitary and compressible construction and formed of foam material.

12. A device for use with a dental impression tray having a tray top, a tray bottom and a tray portion defining a lingual recess to block entry of plaster or other casting material into the lingual recess when a cast is being made in the dental impression tray, said device comprising a block member including an outer engagement surface, said block member being selectively positionable in the lingual recess of a dental impression tray with the outer engagement surface thereof in engagement with the tray portion defining the lingual recess or removable from the lingual recess, said block member being of a size and configuration to be releasably retained in the lingual recess due to engagement between said dental impression tray and said block member, said block member defining a mounting hole for mounting the block member and a dental impression tray connected thereto on a mounting post.

* * * * *